United States Patent [19]
Drolet et al.

[11] Patent Number: 5,874,218
[45] Date of Patent: Feb. 23, 1999

[54] METHOD FOR DETECTING A TARGET COMPOUND IN A SUBSTANCE USING A NUCLEIC ACID LIGAND

[75] Inventors: Dan Drolet; Sumedha D. Jayasena; Larry Gold, all of Boulder, Colo.

[73] Assignee: NeXstar Pharmaceuticals, Inc., Boulder, Colo.

[21] Appl. No.: 628,356

[22] Filed: Apr. 5, 1996

Related U.S. Application Data

[63] Continuation-in-part of Ser. No. 409,442, Mar. 24, 1995, Pat. No. 5,696,249, which is a continuation of Ser. No. 714,131, Jun. 10, 1991, Pat. No. 5,475,096, which is a continuation-in-part of Ser. No. 536,428, Jun. 11, 1990, abandoned.

[51] Int. Cl.$^6$ ............................. C12Q 1/68; C12P 19/34
[52] U.S. Cl. ............................. 435/6; 435/91.2; 935/77; 935/78
[58] Field of Search ..................... 435/6, 91.2; 935/77, 935/78

[56] References Cited

U.S. PATENT DOCUMENTS

| | | | |
|---|---|---|---|
| 5,270,162 | 12/1993 | Gold et al. | 435/6 |
| 5,270,170 | 12/1993 | Schatz et al. | 435/7.37 |
| 5,359,047 | 10/1994 | Donahue et al. | 536/23.5 |
| 5,436,144 | 7/1995 | Stewart et al. | 435/91.2 |
| 5,470,878 | 11/1995 | Michnick et al. | 514/558 |

FOREIGN PATENT DOCUMENTS

| | | | |
|---|---|---|---|
| 2 183 661 | 6/1987 | United Kingdom . | |
| WO 89/06694 | 7/1989 | WIPO . | |
| WO92/214843 | 9/1992 | WIPO | 435/6 |
| WO 93/05182 | 3/1993 | WIPO . | |
| WO 94/01448 | 1/1994 | WIPO . | |

OTHER PUBLICATIONS

Webb et al. (1993) J. Biol. Chem. 268:13994–14002.
Morabito et al. (1991) J. Biol. Chem. 266:9667–72.
Benzinger et al. (1995) Appl. Theroet. Electrophor. 4:161–5.
Tirasophon et al. (1991) Biochem. Biophys. Res. Commun. 175:179–184.
Joyce (1989) Gene 82:83.
Joyce and Inoue (1989) Nucleic Acids Research 17:711.
Ellington and Szostak (1990) Abstract of papers presented at the 1990 meeting on RNA Processing, Cold Spring Harber Laboratory, Cold Spring Harbor, NY, p. 84.
Kinzler and Vogelstein (1989) Nucleic Acids Research 17:3645.
Kramer et al. (1974) J. Mo. Biol. 89:719.
Levisohn and Spiegelman (1969) Proc. Natl. Acad. Sci USA 63:805.
Levisohn and Spiegelman (1968) Proc. Natl. Acad. Sci. USA 60:866.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Robertson and Joyce (1990) Nature 344:467.
Thiesen and Bach (1990) Nucleic Acids Research 18:3203.
Chen et al. (1993) Biochem. and Biophys. Res. Comm. 191:18–25.
Drolet et al. (1996) Nature Biotech. 14:1021–1025.
Kawazoe et al. (1996) Patterned Staining by Fluorescein-–Labeled Oligonucleotides Obtained by In Vitro Selection, Anal. Chem. 68:4309–4311.
Sano et al. (1992) Science 258:120–122.

*Primary Examiner*—Stephanie W. Zitomer
*Assistant Examiner*—Amy Atzel
*Attorney, Agent, or Firm*—Swanson & Bratschun LLC

[57] ABSTRACT

This invention discloses novel detection methods for determining the presence of a target compound in a substance using nucleic acid ligands as detection molecules. Specifically, the substance is bound to a solid support matrix, such as those used in blot procedures, and detection of the target molecule is accomplished using the affinity and specificity of nucleic acid ligands to the target molecule. The method utilized herein for identifying and preparing said nucleic acid ligands is called SELEX. The method of the present invention is additionally useful to isolate the target compounds from the various substances.

12 Claims, 8 Drawing Sheets

METHOD FOR DETECTING A TARGET COMPOUND IN A SUBSTANCE USING A NUCLEIC ACID LIGAND

This application is a continuation-in-part of U.S. patent application Ser. No. 08/409,442, filed Mar. 24, 1995, entitled "Nucleic Acid Ligands", now U.S. Pat. No. 5,696,249 which is a continuation of U.S. patent application Ser. No. 07/714,131, filed Jun. 10, 1991, entitled "Nucleic Acid Ligands", now issued as U.S. Pat. No. 5,475,096, which is a continuation-in-part of U.S. patent application Ser. No. 07/536,428, filed Jun. 11, 1990, entitled "Systematic Evolution of Ligands by Exponential Enrichment", now abandoned.

FIELD OF INVENTION

Described herein are methods for determining the presence of a target compound in a substance using nucleic acid ligands as detection molecules. Specifically, the substance is bound to a solid support matrix, such as those used in blot procedures, and detection of the target molecule is accomplished using the affinity and specificity of nucleic acid ligands to the target molecule. The method utilized herein for identifying and preparing said nucleic acid ligands is called SELEX, an acronym for Systematic Evolution of Ligands by EXponential enrichment. The invention includes high-affinity nucleic acid ligands which bind to various targets which can confirm the presence of target compounds in substances, such as, biological fluids, cell culture media and industrial process fluids and furthermore to determine the absolute target quantity found in the substance. The substance is bound in some fashion to a solid support matrix, such as those used for blot procedures. The process of the invention is additionally useful to isolate the target compounds from the various substances. Particularly preferred target compounds are proteins. Specifically disclosed are assays wherein nucleic acid ligands to human vascular endothelial growth factor (VEGF), human chorionic gonadotropin (ACG) and human thyroid stimulating hormone (hTSH) are used to detect their cognate target compounds in various substances.

BACKGROUND OF THE INVENTION

A method for the in vitro evolution of nucleic acid molecules with highly specific binding to target molecules has been developed. This method, Systematic Evolution of Ligands by EXponential enrichment, termed the SELEX combinatorial chemistry process, is described in U.S. patent application Ser. No. 07/536,428, entitled "Systematic Evolution of Ligands by Exponential Enrichment", now abandoned, U.S. patent application Ser. No. 07/714,131, filed Jun. 10, 1991, entitled "Nucleic Acid Ligands", now U.S. Pat. No. 5,475,096, U.S. patent application Ser. No. 07/931,473, filed Aug. 17, 1992, entitled "Methods For Identifying Nucleic Acid Ligands", now U.S. Pat. No. 5,270,163 (see also WO91/19813), each of which is herein specifically incorporated by reference. Each of these applications, collectively referred to herein as the SELEX Patent Applications, describes a fundamentally novel method for making a nucleic acid ligand to any desired target molecule.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific, high affinity nucleic acid ligands to the target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure", abandoned in favor of U.S. patent application Ser. No. 08/198,670, now U.S. Pat. No. 5,707,796, describes the use of the SELEX process in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands" describes a SELEX-based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine", abandoned in favor of U.S. patent application Ser. No. 08/443,957, now U.S. Pat. No. 5,580,737, describes a method for identifying highly specific nucleic acid ligands able to discriminate between closely related molecules, termed Counter-SELEX. U.S. patent application Ser. No. 08/143,564, filed Oct. 25, 1993, entitled "Systematic Evolution of Ligands by EXponential Enrichment: Solution SELEX", abandoned in favor of U.S. patent application Ser. No. 08/461,069, now U.S. Pat. No. 5,567,588, describes a SELEX-based method which achieves highly efficient partitioning between oligonucleotides having high and low affinity for a target molecule. U.S. patent application Ser. No. 07/964,624, filed Oct. 21, 1992, entitled "Nucleic Acid Ligands to HIV-RT and HIV-1 REV" now U.S. Pat. No. 5,496,938 describes methods for obtaining improved nucleic acid ligands after the SELEX process has been performed. U.S. patent application Ser. No. 08/400,440, filed Mar. 8, 1995, entitled "Systematic Evolution of Ligands by EXponential Enrichment: Chemi-SELEX", now U.S. Pat. No. 5,705,337, describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides", abandoned in favor of U.S. patent application Ser. No. 08/430,709, now U.S. Pat. No. 5,660,985, that describes oligonucleotides containing nucleotide derivatives chemically modified at the 5- and 2'-positions of pyrimidines. U.S. patent application Ser. No. 08/134,028, supra, describes highly specific nucleic acid ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement", describes methods for making various 2'-modified nucleosides.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX", now U.S. Pat. No. 5,637,459, and U.S. patent application Ser. No. 08/234,997, filed Apr. 28, 1994, entitled "Systematic Evolution of Ligands by Exponential Enrichment: Blended SELEX", now U.S. Pat. No. 5,683,867, respectively. These applications allow the combination of the broad array of shapes and other properties, and the efficient amplification and replication properties, of oligonucleotides with the desirable properties of other molecules. Each of the above described patent applications which describe variations of the basic SELEX procedure are specifically incorporated by reference herein in their entirety.

Without question, the SELEX process is very powerful. The nucleic acid ligands obtained by the SELEX process have the ability to act in many capacities. One of the capacities that nucleic acid ligands possess is the ability to bind specifically to a target compound.

Ligands derived by the SELEX process have been used in other diagnostic applications, including in U.S. patent application Ser. No. 08/487,425, filed Jun. 7, 1995, entitled "Enzyme Linked Oligonucleotide Assays ELONAS" and U.S. patent application Ser. No. 08/479,729, filed Jun. 7, 1995, entitled "Use of Nucleic Acid Ligands in Flow Cytometry", both of which are herein incorporated by reference in their entirety.

Specific and high affinity molecular recognition is critical for diagnostic applications. Until recently, engineering of molecules that recognize targets has been mainly limited to proteins. Protein molecules that recognize a specific target have typically been generated as antibodies. As a result, antibodies have received a central role in the development of analytical and separation methods that are currently employed. The methods which primarily use antibodies include, immunometric assays, such as enzyme-linked immunosorbent assays (ELISAs), radioimmunoassays, flow cytometry diagnostics, blotting applications, fluorescent anisotropy, membrane assays, biosensors, etc.

Blotting applications are currently being used as confirmatory diagnostics tests for various disease states, including HIV and Hepatitis C. Blotting applications are also frequently used in the research laboratory.

Immunometric assays have been found to be particularly well suited for the detection of polyvalent targets or antigens, i.e., antigenic substances that are able to complex with two or more antibodies at the same time. Such assays typically employ a quantity of unlabelled antibody bound to a solid support that is insoluble in the fluid being tested and a quantity of soluble antibody bearing a label such as an enzyme or a radioactive isotope that permits detection and/or a quantitative estimate of the ternary complex formed between solid phase antibody, antigen and labeled antibody. Details regarding immunometric assays are provided in U.S. Pat. No. 4,486,530.

Immunoblots have recently been used as diagnostic and research tools. A major advance in the analysis of protein-nucleic acid interactions occurred in 1980, when Bowen et al. (Nucl. Acids Res. (1980) 8:1–20) established a method to detect protein-DNA interactions by binding labeled DNA to proteins which had been separated by SDS-PAGE and transferred to nitrocellulose ("Southwestern blotting"). This procedure was extended to protein-RNA binding ("Northwestern blotting") by demonstrating protein binding to $^{125}$I-labeled Rous sarcoma virus RNA. Most applications of Northwestern blotting have been performed on purified proteins and RNA. There are few examples of the application of Northwestern blotting to detect interactions between specific proteins and mature mRNAs, even though these interactions are important in the translational control of gene expression. There are even fewer examples of the use of the Northwestern blotting method to detect generalized protein-mRNA interactions. One reason for this is that the Northwestern blotting procedure is difficult to apply in a more generalized manner, as the application of the method to search for RNA-binding proteins in the context of a population of hundreds or thousands of proteins is usually confounded by high backgrounds and lack of reproducibility.

An immunoblot is a sensitive immunoassay method for determining whether a substance contains a certain target. Usually an antigen is detected using an antibody specific for the antigen by means of a detection enzyme chemically coupled to the antibody or some other species that has a detectable property such as radioactivity, fluorescence, etc. Typically, a substance which may or may not contain the target compound of interest is attached to a solid support. The matrix-bound substance is contacted with an antibody. After washing, a detection system indicates whether an interaction between the substance and the antibody has occurred. The detection system can be any detection system known to one of ordinary skill in the art, and can include, but is not limited to, enzyme-linked nucleic acid ligands, radio-labeled nucleic acid ligands, enzyme-linked secondary antibody or universal antibody (Protein A), and chemiluminescence detection systems.

In addition to antibodies, oligonucleotides are also being used in diagnostics, but in a different manner. Sequence information of oligonucleotide probes is used to specifically target genomic complementary base sequences in techniques such as Southern blotting, in situ hybridization and polymerase chain reaction (PCR)-based amplifications. However, in these processes information stored in an oligonucleotide is only generally used to detect nucleic acid molecules, and naturally occurring nucleic acid binding proteins. The information content (linear sequence) of nucleic acids predominantly relies on Watson/Crick base pairing and can only discriminate among DNAs and RNAs or the sequence specific nucleic acid binding proteins.

Currently, oligonucleotides are being used in a western blotting format (Northwestern blots) only for the detection of naturally occurring oligonucleotide binding proteins. Specific oligonucleotide probes are used to specifically detect sequence specific or non-sequence dependent nucleic acid binding proteins (Chen, et al., BBRC (1993) 191:18–25).

Diagnostic nucleic acids known to date and most antibodies are known to recognize linear epitopes within a nucleic acid or protein, respectively. Most antibodies are known to recognize linear epitopes within a protein, presumably due to the presentation of peptide fragments by antigen-presenting cells. However, in the SELEX process an intact protein is repeatedly presented to pools of oligonucleotides increasingly enriched in oligonucleotides having an affinity to the intact protein. Hence, SELEX-derived oligonucleotide ligands tend to recognize conformational epitopes. Relying on structural content (three-dimensional structures), nucleic acid ligands can be used in diagnostic applications for any type of target. Before the SELEX process, the structural content of nucleic acids was essentially not appreciated and there was no way to utilize the structural capabilities of nucleic acids in diagnostics.

The use of nucleic acid ligands in blot-type diagnostic assays, which were previously believed to depend on antibody recognition, has not been demonstrated thus far. Ligand binding information stored in the three dimensional structure of an oligonucleotide is useful for the detection of target molecules in substances, including protein targets that do not normally function to bind nucleic acids. The present invention demonstrates that oligonucleotides that bind with high affinity to their cognate target compounds can replace antibodies in a matrix-bound target detection format. More specifically, SELEX-derived oligonucleotides that bind with high affinity to human VEGF, hCG and hTSH can replace antibodies in a western blot format.

SUMMARY OF INVENTION

The present invention includes novel diagnostic methods wherein a substance is bound to a solid support and a nucleic acid ligand is used to determine whether a target compound is present in the substance. A preferred method of the present invention includes blotting procedures employing nucleic acid ligands. More specifically, the present invention includes a blotting procedure employing novel nucleic acid ligands as the detection molecule.

The present invention provides a method for detecting the presence of a target compound in a substance which may contain said target compound comprising a) attaching a substance which may contain said target compound to a solid support; b) exposing said substance to a nucleic acid ligand to said target compound wherein said nucleic acid ligand binds to said target compound forming a nucleic acid ligand:target compound complex; and c) detecting said nucleic acid ligand:target compound complex.

More specifically, the nucleic acid ligand based methods of the present invention are useful for detecting VEGF, hCG, and hTSH.

DETAILED DESCRIPTION OF THE INVENTION

Figure 1:
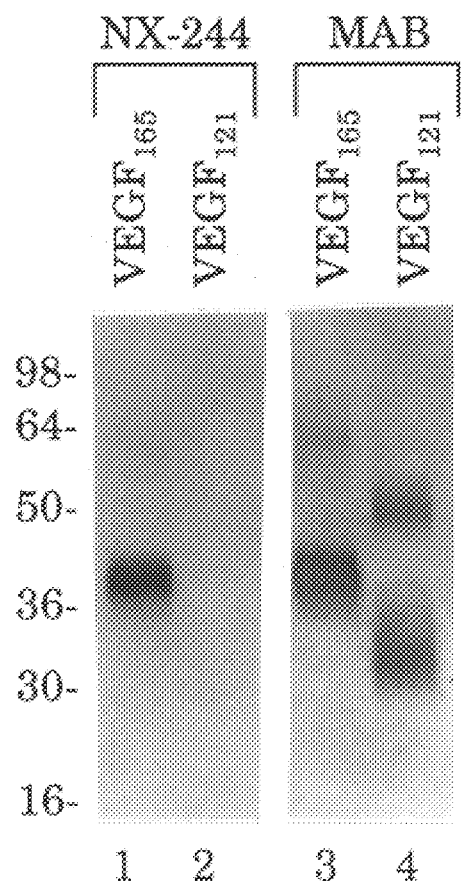
FIG. 1 depicts the result of a protein blot assay that shows that the SELEX-derived oligonucleotide NX-244 (SEQ ID NO: 1) recognizes $VEGF_{165}$, but not $VEGF_{121}$. The protein blot used NX-244 or a monoclonal antibody (MAB) as the detect probe. Lanes 1 and 3 contain 150 ng of $VEGF_{165}$ while lanes 2 and 4 contain 150 ng of $VEGF_{121}$. The positions of the protein molecular weight markers in Kilodaltons are indicated.

This application describes the use of high-affinity nucleic acid ligands to various targets in any matrix-bound target detection protocol, such as immunoblot protocols. Nucleic acid ligand is defined herein as a non-naturally occurring nucleic acid having a specific binding affinity for a target compound, such target compound being a three dimensional chemical structure other than a polynucleotide that binds to the nucleic acid ligand through a mechanism which predominantly depends on Watson/Crick base pairing or triple helix binding, and wherein the nucleic acid ligand is not a nucleic acid having the known physiological function of being bound by the target compound. In the preferred embodiments, the nucleic acid ligand is a single stranded nucleic acid ligand.

In the preferred embodiment, the nucleic acid ligands are identified through the method known as the SELEX process. The SELEX process is described in U.S. patent application Ser. No. 07/536,428, entitled *Systematic Evolution of Ligands by EXponential Enrichment*, now abandoned, U.S. patent application Ser. No. 07/714,131, filed Jun. 10, 1991, entitled *Nucleic Acid Ligands,* now U.S. Pat. No. 5,475,096, U.S. patent application Ser. No. 07/931,473, filed Aug. 17, 1992, entitled *Methods for Identifying Nucleic Acid Ligands*, now U.S. Pat. No. 5,270,163, (see also WO91/19813). These applications, each specifically incorporated herein by reference, are collectively called the SELEX Patent Applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with a lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained each during partitioning step.

4) Those nucleic acids selected during partitioning as having relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate an enriched candidate mixture. The SELEX Patent Applications also describe ligands obtained to a number of target species, including both protein targets where the protein is and is not a nucleic acid binding protein. The SELEX Patent Applications describe a number of uses for nucleic acid ligands including numerous therapeutic and diagnostic uses.

The SELEX process provides high affinity ligands of a target molecule. This represents a singular achievement that is unprecedented in the field of nucleic acids research. Affinities of SELEX-derived nucleic acid ligands often lie in the same range observed with structurally much larger monoclonal antibodies.

In one embodiment, it is preferred that the nucleic acid ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

Until recently, the design and production of biopolymers capable of molecular recognition has been mainly limited to proteins (antibodies). However, the SELEX process allows the identification of nucleic acid sequences that recognize target molecules with high affinity and specificity. This process is faster than the generation of monoclonal antibodies and does not require the use of animals as required to generate antibodies. Once the sequence of a high-affinity ligand is identified, the material can be chemically synthesized in large quantities. This is a definite advantage over processing and storage of antibody-producing cell lines.

Additionally, specific and high-affinity nucleic acid ligands can be generated for targets that are not readily immunogenic. This adds a new dimension to the types of information that can be gained from this diagnostic application. Clearly, target compounds that have never before been the subject of successful diagnostic assays can be detected using this new procedure.

The nucleic acid ligands of the present invention offer additional advantages over antibodies. Nucleic acid ligands may have a greater specificity for target compounds than the specificity exhibited by conventional antibodies as demonstrated in U.S. patent application Ser. No. 08/134,028, filed Oct. 7, 1993, entitled "High Affinity Nucleic Acid Ligands the Discriminate Between Theophylline and Caffeine," abandoned in favor of U.S. patent application Ser. No. 08/443,957, now U.S. Pat. No. 5,580,737 which is herein incorporated by reference. Whereas antibodies generally have multiple binding sites, only two of which are specific for a target compound, the entire molecule of the nucleic acid ligand may be utilized for the binding of a target compound. The nucleic acid ligands of the invention may be identified and prepared to contain a single specific binding site. Thus, there is potentially far less nonspecific binding of nontarget compounds when nucleic acid ligands are utilized in immunoassays. This provides a more reliable detection signal for the presence of target compounds.

One of the biggest advantages of the present invention is that the relatively small oligonucleotides of known sequence can easily be replicated in many laboratories and, unlike antibodies, will have the same binding properties. Further, the oligonucleotides can be easily modified to include not only biotins, but other equally useful moieties such as fluorochromes such as fluorescein, radioisotopes such as phosphorous 32 ($^{32}$p), steroids such as cholesterol or digoxygenin and peptides. The various modifications allow the choice of a detection moiety. It is possible to covalently or even non-covalently link the oligonucleotide directly to an reporter enzyme such as horseradish peroxidase, alkaline phosphatase or B-galactosidase, among others.

An additional advantage of utilizing nucleic acid ligands in inmmunoassays is that certain target compounds will bind to nucleic acid ligands, but will not bind to antibodies. Examples of such compounds are small molecules that cannot be conjugated to larger proteins to illicit an immune response in mice or rabbits such as glucose, and catecholamines such as epinephrine, norepinephrine and a 3-deoxy-D-manno-octulosonic acid (a trisaccharide specific for Chlamydia organisms).

Furthermore, due to the smaller size (compared to antibodies), nucleic acid ligands are expected to be effective in intracellular staining, i.e., nucleic acid ligands can be used in detecting the expression of target molecules at the cellular level.

The present invention provides a method for detecting the presence of a target compound in a substance which may contain said target compound comprising a) attaching a substance which may contain said target compound to a solid support; b) exposing said substance to a nucleic acid ligand to said target compound wherein said nucleic acid ligand binds to said target compound forming a nucleic acid ligand:target compound complex; and c) detecting said nucleic acid ligand:target compound complex. This invention applies to any solid phase or matrix-bound detection system.

A. Attachment of Substance to Solid Support

The techniques of polyacrylamide gel electrophoresis, protein electroblotting, and immunodetection combine to provide an extremely powerful and sensitive method for the analysis and characterization of substances, including complex protein mixtures. Polyacrylamide gel electrophoresis (one- and two-dimensional PAGE) is one of the most widely used techniques for the analysis and characterization of various substances. The gels can be stained directly and substance components, such as proteins, visualized by several different methods. Electrophoretic transfer of substances, such as proteins separated by PAGE onto the surface of an immobilizing membrane makes them more accessible to various reagents and probes. In the present invention the transferred materials are probed with nucleic acid ligands.

Analysis of such materials includes the identification and characterization of an immobilized antigen by the use of nucleic acid ligands which can be visualized by radiolabeled or enzyme-conjugated nucleic acid ligands or second antibodies. If nucleic acid ligands are affixed to the membrane, they can be identified and characterized by probing with selected proteins. A limitation to this procedure is that if the proteins bound to the membrane become denatured, they may no longer contain the same conformational and structural determinants present in the native protein. Any suitable solid support is useful in the present invention.

The solid supports of the present invention include, but are not limited to, membranes, charged paper, nylon, beads, or virtually any other type of solid support. Several types of transfer membranes are now available. In addition to standard nitrocellulose, which is the most commonly used support, several companies now offer nitrocellulose impregnated with a synthetic support, which improves durability and flexibility without altering performance. Polyvinylidene difluoride (PVDF) membrane is marketed by Millipore (Bedford, Mass.), under the trade name Immobilon. Although its protein-binding capacity is slightly lower than nitrocellulose, it is mechanically stronger and is compatible with many organic solvents. This allows direct protein staining with Coomassie Blue, and direct amino acid composition and sequence analysis of transferred proteins, without interfering with its subsequent use for nucleic acid ligands.

A wide variety of transfer methods have been developed. However, the conditions for optimal transfer and subsequent binding of a specific protein to a membrane must be determined empirically and may vary for different protein samples. Many parameters affect the efficiency of protein transfer, most of which can be easily manipulated. Several types of transfer units are commercially available. The Bio-Rad Transblot unit (Richmond, Calif.), the Hoefer unit (San Francisco, Calif.), and the Electroblot apparatus (E. C. Apparatus Corp., St. Petersburg, Fla.) each require 4–6 liters of buffer per experiment, and are routinely used for the efficient and reproducible transfer of proteins.

The choice of buffer composition depends on the types of gel and membrane selected. Certain procedures specify a Tris-glycine pH 8.3 buffer containing sodium dodecyl sulfate (SDS). Using recirculating, ice-cooled, high ionic strength buffer helps prevent the gel from swelling in the absence of methanol during transfer, which can cause poor resolution of the proteins on the membrane.

Although many variations of electrophoretic transfer of proteins to nitrocellulose have been described, a procedure that omits alcohol from transfer solutions is generally optimal. Because SDS is not rapidly removed from the proteins in the absence of alcohol, the detergent-bound proteins are all initially negatively charged and a more quantitative transfer of proteins is achieved. Furthermore, alcohols or other reagents can alter or modify molecules and may therefore destroy some antigenic determinants. The method described originally by Towbin, et al. (PNAS (1979) 76:4350) as modified by Anderson et al. (Electrophoresis (1982) 3:135) results in efficient and reproducible protein transfer onto either nitrocellulose (Bio-Rad) or PVDF (Millipore). The procedure includes carrying out SDS-PAGE separation of substances, usually proteins (one- or two-dimensional separations, full-size or minigels). It is usually beneficial to include pre-stained molecular weight markers: their separation during electrophoresis, and the efficiency of their electrophoretic transfer onto a membrane, can be monitored visually. A variety of these standards are now commercially available. All blot procedures known to those of ordinary skill in the art are applicable in this invention.

B. Exposure of the Substance to Nucleic Acid Ligands

The immobilized substance must be exposed to the nucleic acid ligand in order for target compound:nucleic acid ligand complexes to form. The procedure for detection of target compound antigens with nucleic acid ligands is compatible with most techniques known to those skilled in the art for immunodetection. Briefly, the procedure can be as described below, or can include variations thereof.

The present invention is compatible with either PVDF or nitrocellulose membranes. A 3–5% solution of nonfat dry milk, bovine serum albumin or the like, efficiently blocks most nonspecific binding sites. However, the carbohydrates present may interfere with binding of a nucleic acid ligand recognizing a carbohydrate determinant. Other common blocking reagents include nonionic detergents such as PVP-40 (polyvinylpyrrolidone, average MW=40,000) and Tween 20. Immediately after protein transfer is completed, the membrane is placed (protein side up) in a dish and incubated with 100–150 ml blocking solution and agitated at room temperature for 6–24 hours on a rotating or shaking platform. The membrane is then washed two times with 100–150 ml TBS/azide for 20 min. each. The nucleic acid ligand is dissolved in blocking solution, in a volume that will just completely cover the membrane. The amount of nucleic acid ligand will depend on the nucleic acid ligand affinity and can range from 20 ml (1 to 10 ml in 60 ml of blocking solution). The nucleic acid ligand solution is added to the membrane and incubated with vigorous shaking for about 6 hours. The specific incubation times may be reduced, depending on the titer and nature of the nucleic acid ligand.

C. Detection of the Target Compound:Nucleic Acid Ligand Complex

Once the target compound:nucleic acid ligand complex has formed, the complex must be detected. The nucleic acid ligand comprises a detection system which may comprise one of a wide array of known chemical entities. The detection system may include the use of an enzyme, a fluorophore, a radiolabel, an antibody, etc. The various detection systems are well known to those skilled in the art. In the preferred embodiment, the nucleic acid ligand further comprises an enzyme.

The attachment of a suitable detection moiety such as an enzyme or a fluorophore to nucleic acid ligands is not problematic and in some cases fluorophores can be attached during the chemical synthesis of the ligand itself. The use of bioluminescent and chemiluminescent substrates allows the detection of target compound concentrations in the $10^{-15}$–$10^{-19}$M range. The sensitivity of the assay may be further increased by using bioluminescence or chemiluminescence when nucleic acid ligands are attached to alkaline phosphatase (AP).

In another embodiment, the detection system can be PCR amplification of the nucleic acid ligand which is a part of the nucleic acid ligand:target compound complex. PCR amplification methods are well known to those skilled in the art. In this embodiment, the PCR primers used for amplification can also comprise various detection moieties or reporter molecules. The reporter molecules can be enzymes, biotins, or other known reporter groups.

Target compounds, or antigens, may be visualized directly on the transfer membrane using an enzyme-conjugated nucleic acid ligand. The enzymes most commonly used in this procedure, alkaline phosphatase and horseradish peroxidase, form a colored product which can be detected by visual inspection of the membrane. The high sensitivity of this type of reagent has both advantages and disadvantages. Results are obtained quickly, but the use of an extremely sensitive detection method can be confusing, especially if the background staining level is high. If the signal-to-noise ratio is too low or the optimal amount of protein is not immobilized on the membrane, and the desired information cannot be obtained; the membrane can not easily be reprobed or stripped. However if a radiolabel is used, the time of autoradiographic exposure can be varied to obtain the optimal signal, the membrane can be reprobed easily, and with less buildup of background signal than is possible with enzyme-conjugated detection. However, the speed of detection is often an overriding concern, and the enzyme-conjugated protocol may be the method of choice.

Another embodiment of the invention includes nucleic acid ligand:protein blots that include a gel shift assay. A gel shift assay is a powerful method for the analysis of nucleic acid-protein interactions. The assay itself is simple. Nucleic acid and protein are mixed together, the solution subjected to electrophoresis through polyacrylamide, and the gel is then analyzed for nucleic acid, usually by autoradiography of radiolabeled nucleic acid. Binding of the protein to the nucleic acid can result in a complex that has a different electrophoretic mobility from the free nucleic acid. In general, the mobility of the complex is retarded relative to the unbound nucleic acid ligand and thus the assay is often called gel retardation. However, with circular nucleic acid substrates (typically, minicircles of 200–400 bp), the nucleic acid ligand:protein complex can migrate faster than the free nucleic acid ligand. The separation of the complex from the free nucleic acid ligand, and therefore the detection of the complex, is dependent on a variety of factors. These must be determined experimentally for each system. However, the ease with which the assay can be performed means that the optimal conditions can be discovered quickly. Factors that influence the electrophoretic mobility of nucleic acid ligand:protein complexes include the molecular weight of the protein and nucleic acid ligand, the ionic strength and the pH of the electrophoresis buffer, the concentration of the gel matrix, and the temperature.

The principle embodied in the gel shift assay is that the entry of the mixture of free nucleic acid ligand and nucleic acid ligand:protein complex into the gel matrix results in the physical separation of the two species. In the subsequent electrophoresis, the protein can make no difference to the mobility of the free nucleic acid ligand and, provided that the bound nucleic acid ligand remains associated with the protein, it will have a characteristic mobility. The gel matrix may stabilize the complex by hindering the diffusion of the protein away from the nucleic acid ligand, although it has been shown that complexes can reversibly dissociate then reassociate within the gel. However, even if the bound nucleic acid ligand dissociates from the protein during electrophoresis, it can never "catch up" with the nucleic acid ligand that was free at the start of the run. Thus, the method has the potential of "freezing" the equilibrium between bound and free nucleic acid ligand at the moment of entry into the gel. The concentration of each species can then be determined. Assays of this type can yield the equilibrium constant for the binding of the protein to its nucleic acid ligand and also the kinetics of the interaction, the latter by analyzing samples at different times after mixing the nucleic acid ligand with the protein.

The preferred use of the present invention is for the detection of target compounds in samples of substances for the clinical diagnosis of physiologic conditions. The substance is usually a biological material which may or may not contain the target compound of interest. Such biological materials include blood, plasma, serum, sputum, urine, semen, cerebrospinal fluid, bronchial aspirate, and macerated tissue. The target compound is typically a protein, carbohydrate or lipid derived from bacterial, fungal, viral, plant or animal sources. The immunoblots of the present invention are useful for both human and veterinary diagnostics. Other samples which may be assayed with the immunoblots of the invention include foods and environmental discharges such as liquid wastes.

Example 1 demonstrates that a SELEX process derived nucleic acid ligand can be used to reliably detect hVEGF, a factor that does not naturally bind nucleic acids, in a Western blot format.

Example 2 demonstrates that a SELEX process derived nucleic acid ligand can detect hVEGF in a mixture of whole cell bacterial lysates in a blot format.

Examples 3 and 4 demonstrate that a SELEX process derived nucleic acid ligand can detect hTSH and hCG, respectively, in a dot blot format.

EXAMPLE 1

Detection of Purified hVEGF in a Blot Format

This Example demonstrates that a SELEX derived oligonucleotide can be used to reliably detect hVEGF, a factor that does not naturally bind nucleic acids, in a protein blot format. VEGF is a potent endothelial cell mitogen and angiogenic factor. Angiogenesis is required for several normal and abnormal physiologic processes including solid tumor growth and wound healing. In fact, administration of anti-VEGF antibodies can inhibit tumor growth in vivo. Although VEGF levels in normal and pathophysiological states are under current investigation, knowledge of its distribution and production under most circumstances is still very limited.

The assay described herein was performed using a detect reagent consisting of a fluorescein tagged SELEX process derived nucleic acid ligand which binds to human VEGF with a Kd of 140 pM (SEQ ID NO: 1). This oligonucleotide, NX-244, was modified to be nuclease resistant (Green, et al., 1995, Chemistry & Biology 2:683–695, incorporated hereby by this reference). After a final incubation with alkaline phosphatase conjugated anti-fluorescein fab fragments, signal was generated using a chemiluminescent alkaline phosphatase detection system or colored dye detection system.

Molecular weight standards (Bio-Rad) and 150 ng samples of $hVEGF_{165}$ and $hVEGF_{12}$, were resolved using 1 mm thick 12% Tris-glycine SDS polyacrylamide gels (Novex; San Diego, Calif.). Electrophoresis was performed for 90 minutes at 125 volts. The resolved proteins were then transferred to Immobilon-P membranes (Millipore Corp.; Bedford, Mass.). Transfer was allowed to proceed for 2 hours at 40 volts using a NOVEX western transfer apparatus according to the manufacturer's instructions (Novex Inc.). The transfer buffer consisted of 25 mM Tris-HCl, 192 mM glycine, 20% methanol, 0.1% SDS, pH 8.3. Membranes were blocked overnight at room temperature with Superblock Blocking buffer in TBS (Pierce Chemical Company). The next day the membrane was allowed to incubate for two hours in wash buffer (see above) containing either a 0.5 mg/ml solution of the VEGF specific monoclonal antibody (Clone 26503.11) or a 1 mg/ml solution of a fluorescein tagged nucleic acid ligand to VEGF, NX-244 (SEQ ID NO: 1). Membranes were then washed three times with 10 ml of wash buffer. The appropriate detect reagent, either a 1:1000 dilution in wash buffer of Alkaline Phosphatase (AP)-conjugated rabbit anti-mouse antibody (Pierce Chemical Co.) or a 1:1000 dilution in wash buffer of AP-conjugated anti-fluorescein FAB fragments (Boehringer Mannheim), was added. Following a one hour incubation at room temperature, the membrane was washed as before followed by two additional washes with 10 ml of deionized water. Finally, 10 ml of Western Blue substrate was added (Promega Corp., Madison, Wis.). At the desired intensity, color development was stopped by rinsing with water. Membranes were dried and photographed.

As shown in FIG. 1, when the blot was probed with the monoclonal antibody both forms of VEGF could be detected. However, when the blot was probed with NX-244, only $VEGF_{165}$ could be detected. Therefore, these results demonstrate that a SELEX derived oligonucleotide can be used in a western blotting format and that the specificity of the oligonucleotide can be complementary to the specificity of monoclonal antibodies. In a similar protein blotting experiment, NX-244 also did not detect the single chain of $VEGF_{65}$ when the dimer was reduced, using 10 mM dithiothreitol, prior to electrophoresis (data not shown).

EXAMPLE 2

Detection of hVEGF Spiked into Bacterial Whole Cell Protein Lysates in a Blot Format In this example, various amounts of $VEGF_{165}$, were spiked into 10 mg aliquots of an *E. coli* whole cell lysate. These complex protein mixtures were resolved by SDS polyacrylamide gel electrophoresis, electrophoretically transferred to a membrane and blotted as described in Example 1 except that a different SELEX derived nucleic acid ligand was used (NX-295)(SEQ ID NO: 2) and a chemiluminescent detection system was used to expose a film.

Human $VEGF_{165}$ samples were spiked at various concentrations ranging from 100 ng to 0.75 ng into 10 mg of an acetone precipitated total *E. coli* cell lysate and heated for 5 minutes at 80 degrees centigrade. The protein mixtures were resolved, along with molecular weight markers (Novex), using 1 mm thick 12% Tris-glycine polyacrylamide gels (Novex). Electrophoresis was performed at 125 volts per gel for 1.5 hours. The resolved proteins were transferred to Immobilon-P membranes for 2 hours at 30 volts as previously described except without the SDS in the transfer buffer. Membranes were blocked in a buffer containing 1X TBS, 2 g/L BSA, 100 mg/L yeast tRNA and 0.05% tween 20 for 5 minutes at room temperature and then rinsed once with incubation buffer (1X TBS, 0.5 g/L casein, 100 mg/L yeast tRNA and 0.05% tween 20). Ten milliliters of a 2 mg/ml solution of NX-295 in incubation buffer was added and allowed to incubate for 1 hour at room temperature. The blot was then subjected to four washes (30 sec. each) with incubation buffer. A 1:2000 dilution of Fluorx-AP (Alkaline phosphatase conjugated anti-fluorescein antibody; Novex, Inc.) in incubation buffer was added and allowed to incubate for 30 minutes at room temperature. The membranes were then washed as before followed by two additional wash steps using Milli-Q water. A final 5 minute incubation of the membrane was performed in 10 ml of DEA buffer (1% w/v diethanolamine pH 10, 1 mM magnesium chloride, 0.02% sodium azide, and 1% v/v CSPD). Following this incubation, the membrane was wrapped in plastic wrap and exposed to film (BioMax; Kodak) for 10 minutes. After developing the film, densitometry was performed using a Personal Densitometer (Molecular Dynamics), according to the manufacturers directions. Data were fit to a one site binding hyperbola model using GraphPad Prism (GraphPad Prism Software).

Figure 2:
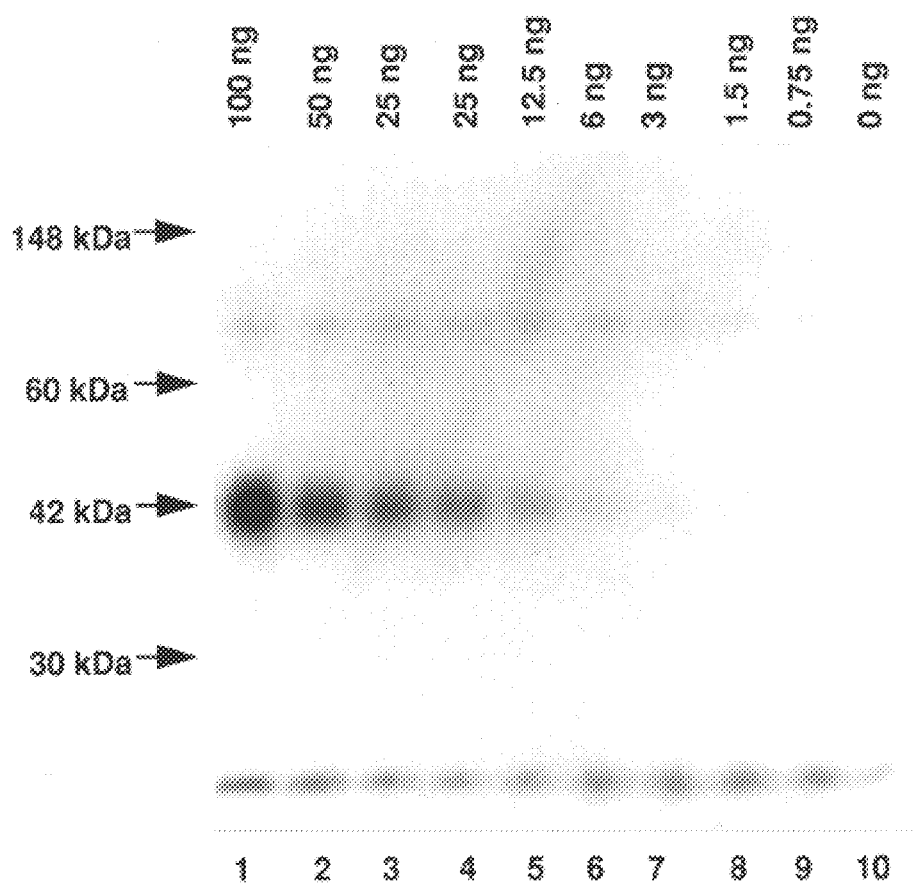
FIG. 2 depicts the result of a protein blot assay in which 10 mg aliquots of whole cell bacterial lysates were spiked with decreasing levels of human $VEGF_{165}$. The amount of $VEGF_{165}$ spiked into the bacterial extract is indicated in nanograms (ng), at the top of each lane. The positions of the protein molecular weight markers in kilodaltons is indicated on the left.
Figure 3:
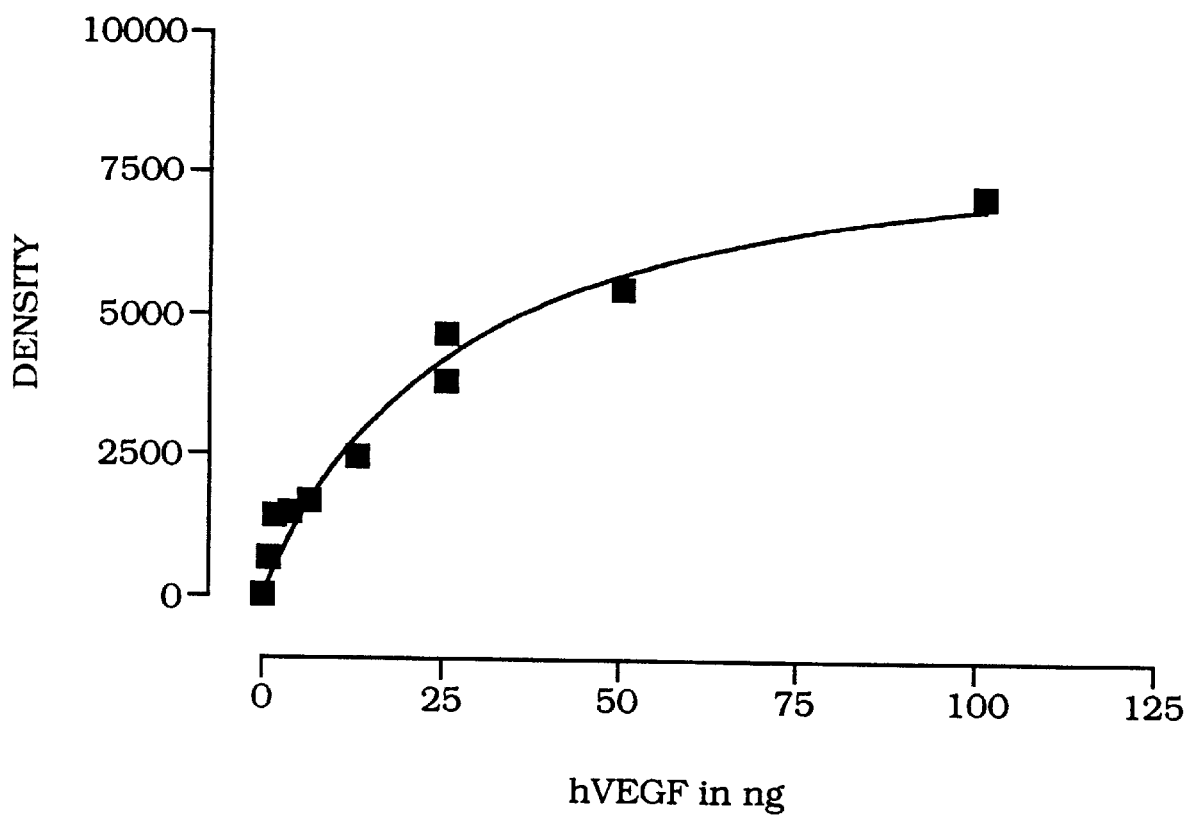
FIG. 3 depicts the plot of density versus $VEGF_{165}$ concentration obtained from the blot shown in FIG. 2 as read on a Personal Densitometer 100 Minute Exposures. Density on the film is proportional to the amount of $VEGF_{165}$ loaded. Thus the technique can be used to quantify VEGF levels in a complex mixture.

Shown in FIG. 2 are the results of this analysis. The oligonucleotide, NX-295, was clearly able to detect VEGF in this complex mixture. Although the oligonucleotide did bind to some bacterial proteins, this did not effect the ability to quantify the hVEGF level on the membrane. Such non-specific binding is sometimes observed for antibodies as well. FIG. 3 shows the result of a densitometry scan of the film shown in FIG. 2. The shape of this curve was a typical saturation binding isotherm and as little as 1 ng of VEGF could be detected in a lane.

EXAMPLE 3

Detection of hTSH using a Dot Blot Format

Using a dot blot format, native hTSH was detected with a radiolabeled nucleic acid ligand to hTSH as a signal. hTSH is a glycohormone which stimulates the synthesis of thyroid hormones. Measurements of serum hTSH levels are important in the diagnosis of both pituitary and thyroid disorders such as hyperthyroidism and hypothyroidism. A SELEX-derived nucleic acid ligand which binds hTSH, ligand T-15 (SEQ ID NO: 3), as described in U.S. patent application Ser. No. 08/488,402, filed Jun. 7, 1995, entitled "High Affinity Oligonucleotide Ligands to Chorionic Gonadotropin Hormone and related Glycoprotein Hormones" (incorporated hereby by this reference) can act as detector in a blot assay.

Ligand T-15 is a high affinity ligand, having a Kd of 2.5 nM for its interaction with hTSH. The specificity of ligand T-15 for hTSH has been demonstrated by its inability to bind with high affinity to hCG, hLS and hFSH, especially in the presence of competing tRNA. These results were obtained under direct selection conditions, where no specific counterselection against ligands with affinity for closely related members of the glycohormone family was incorporated.

Many of the materials and methods are similar to those employed in Example 1. Deoxyoligonucleotides were synthesized by standard cyanoethyl phosphoramidite chemistry. 2'-$NH_2$-modified UTP and CTP were synthesized by known methods. hTSH ($M_r$=27,700; 9IU (International Units)/mg was from Becton Dickinson; Research Triangle Park, N.C.).

An RNA ligand that binds to hTSH with high affinity was used to detect the presence of hTSH in a dot blot format. The RNA ligand was identified as described in U.S. patent application Ser. No. 08/488,402, filed Jun. 7, 1995, entitled "High Affinity Oligonucleotide Ligands to Chorionic Gonadotropin Hormone and related Glycoprotein Hormones", which is incorporated herein by reference in its entirety. The RNA ligand was designated T-15 and had the following sequence 5'-GGGAGGACGAUGCGGAUGUUGGCAG-CA GGGUCCGACGGCGUAACCUUGCCAGCUGCAG-ACGACUCGCCCGA-3' (SEQ ID NO: 3). All cytosines and uridines were modified at the 2'-position with an $NH_2$ group in place of the OH group.

hTSH was suspended in TEM buffer (300 ml) containing 0.1% hSA (w/v) and applied to pre-wetted nitrocellulose filters (0.45 micron; BioRad) under suction. Gel-purified, internally labeled nucleic acid ligand T-15 (SEQ ID NO: 3) was then applied to the blots in 50 ml of TEM buffer (0.2 pmoles/ml) and filtered gently. Filters were immediately washed three times with 300 ml of 0.5M urea in the same buffer. The blots were dried and analyzed with a phosphorimager and by autoradiography.

Figure 4:
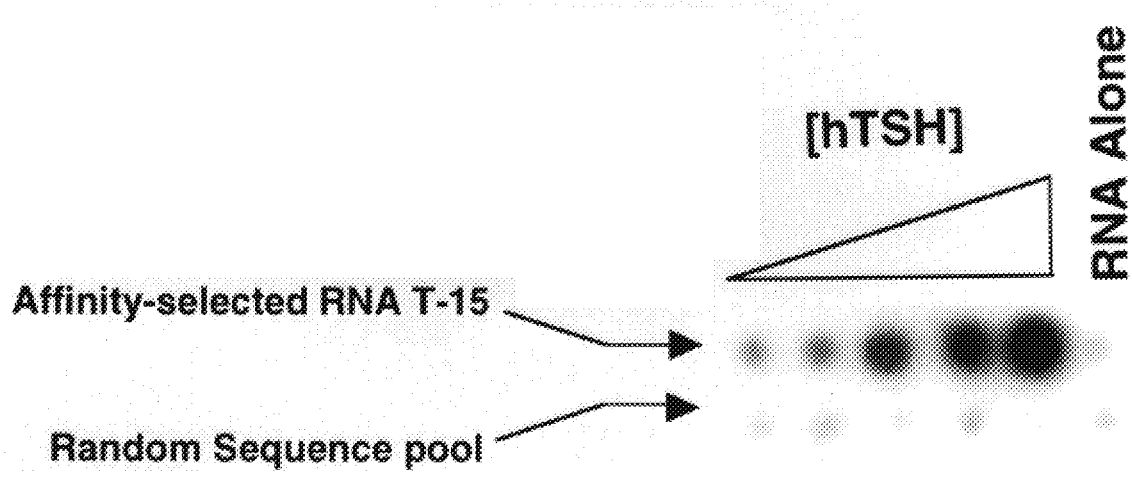
FIG. 4 depicts the result of a protein blot assay showing that a nucleic acid ligand to hTSH recognizes hTSH, but a selected oligonucleotide pool does not.
Figure 5:
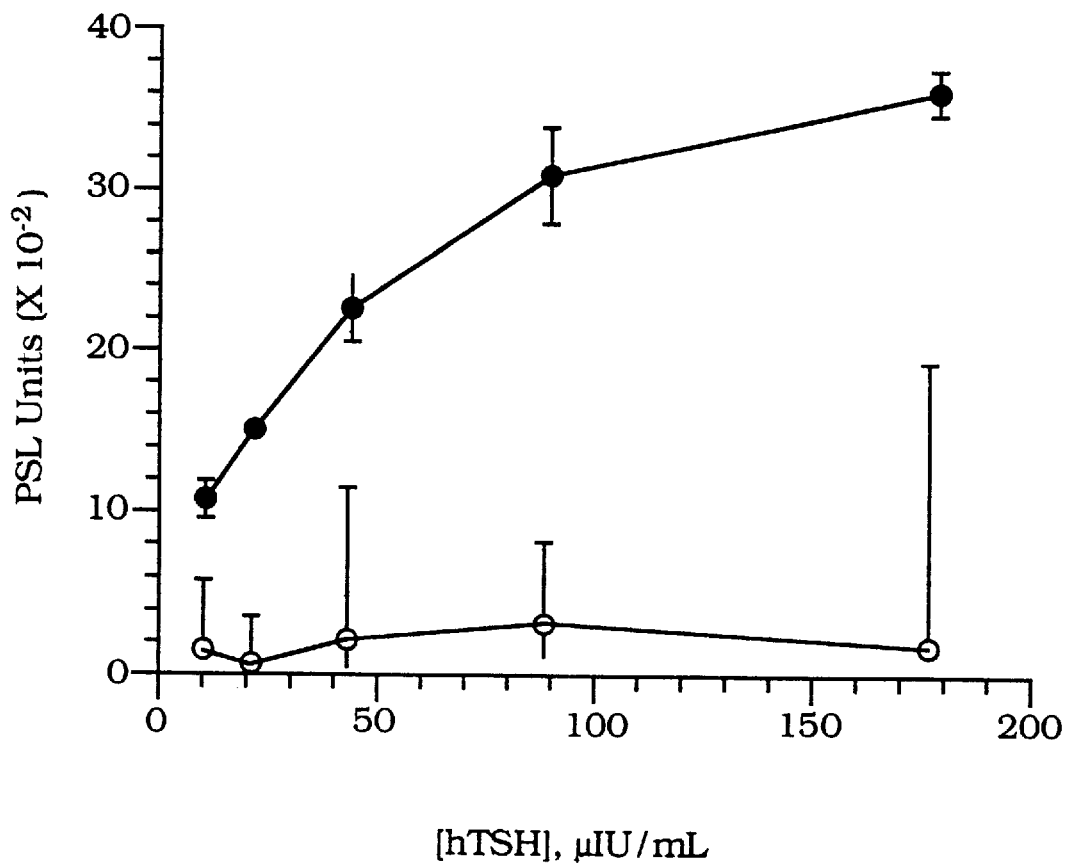
FIG. 5 depicts the phosphorimager quantitation of the signal of an hTSH dot blot as a function of the input concentration of hTSH.

The results wherein different concentrations of hTSH (from 800 nM (177 mIU/ml) to 50 nM (11 mIU/ml)) blotted on a nitrocellulose membrane were detected by radiolabeled nucleic acid ligand T-15 are shown in FIG. 4. Very low levels of background binding of RNA to nitrocellulose filters in the absence of hTSH (but with hSA in the buffer) was accomplished by washing blots with 0.5M urea in the binding buffer. This step eliminated most nonspecific binding, yet leaving specific binding of ligand T-15 to hTSH largely unaffected. Phosphorimager quantitation of the signal as a function of the input concentration of hTSH is shown in FIG. 5. The radioactive signal obtained with the radiolabeled unselected random sequence pool (used as a control) did not correlate with the amount of hTSH on the blot (FIGS. 4 and 5). However, with the affinity-selected radiolabeled ligand T-15, the radioactive signal on the blot correlated with the concentration of hTSH used. There is a linear relationship between the radioactive signal and the amount of hTSH up to 100 mIU/ml; the signal saturates above this concentration.

EXAMPLE 4

Detection of hCG using a Dot Blot Format

This example demonstrates that a nucleic acid ligand to hCG can replace an antibody in an immunoblot format. A SELEX-derived nucleic acid ligand which binds hCG, ligand H-42 (SEQ ID NO:4), as described in U.S. patent application Ser. No. 08/488,402, filed Jun. 7, 1995, entitled "High-Affinity Oligonucleotide Ligands to Chronic Gonadotropin Hormone and related Glycoprotein Hormones" (incorporated herein by this reference) can act as a detector in blot assay. Test urine (obtained from pregnant individuals) and control urine (obtained from males) samples were pre-filtered through 0.2 mm polysulfone filters (Gelman Sciences) to remove particulate matter. hCG suspended in control urine to various concentrations (300 ml) was blotted onto pre-wetted nitrocellulose filters (from BioRad) under vacuum. Radiolabeled nucleic acid ligand to hCG, H-42 RNA (SEQ ID NO: 4)(100 ml of 1 pmole/ml) was then added to blots and filtered. Blots were immediately washed two times with 300 ml of TEM buffer. The blots were dried and analyzed by autoradiography and phosphorimager (Fuji).

Figure 6:
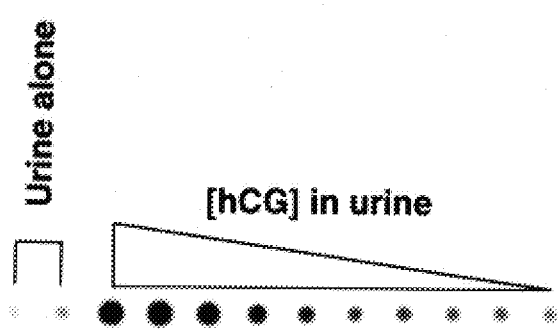
FIG. 6 depicts the results of a dot blot assay in which a male urine sample was spiked with varying amounts of hCG and detected by a radiolabeled nucleic acid ligand to hCG.
Figure 7:
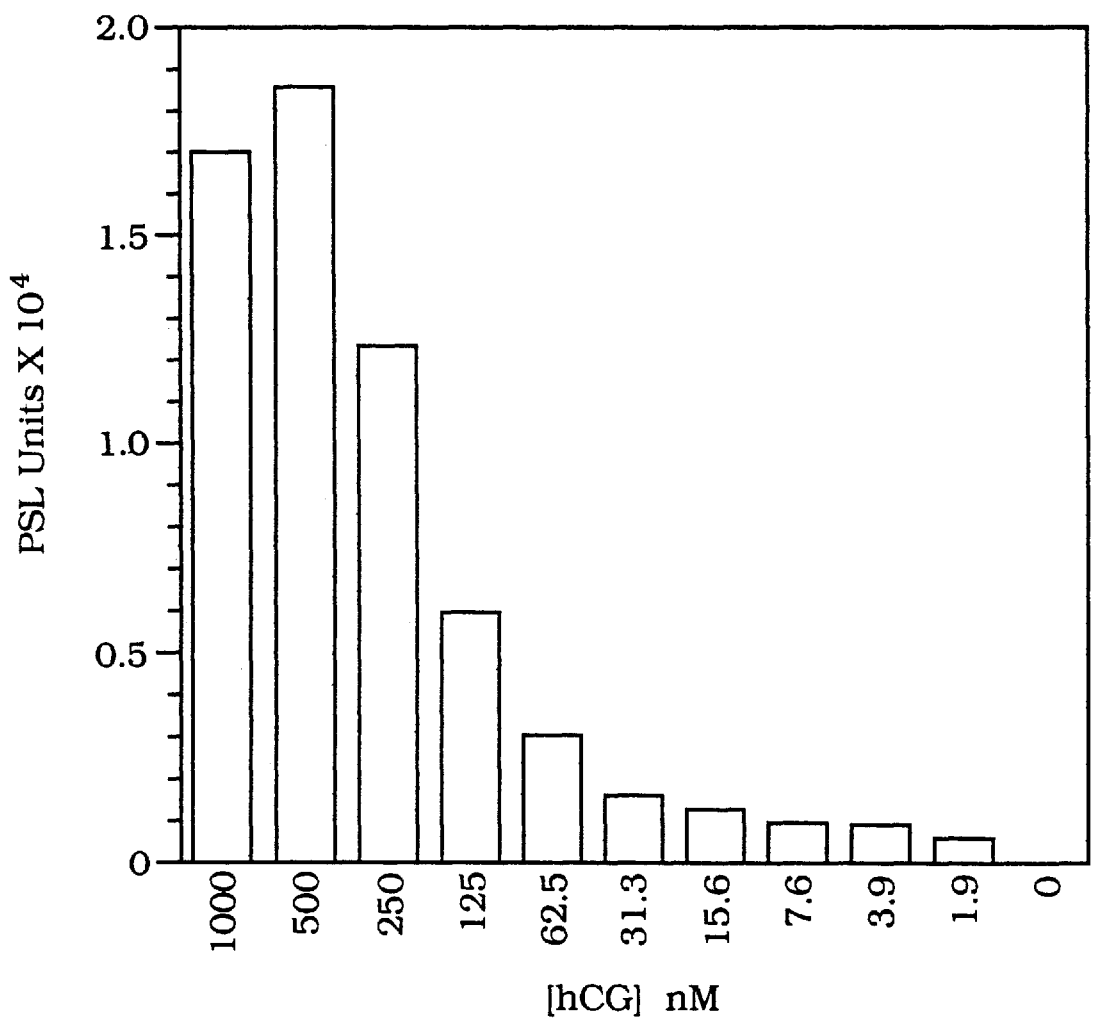
FIG. 7 depicts the quantitation of radiolabeled nucleic acid ligand as it correlates with the concentration of hCG in the blot assay.
Figure 8:
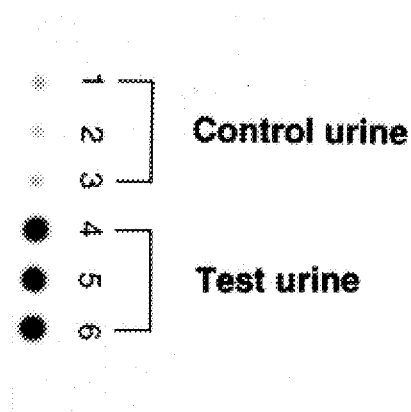
FIG. 8 depicts the results of an hCG dot blot assay of control urine and pregnant female urine.

In preliminary studies, anti-hCG antibodies were first applied to nitrocellulose blots to capture hCG and subsequently the radiolabeled RNA was used to detect the hormone. Such anti-hCG antibodies were required only if hCG was suspended in a buffer. However, if hCG in urine was used there was no significant difference in the signal in the presence and absence of antibodies. This may be due to the presence of other proteins in urine that serve as nonspecific carriers, effectively retaining hCG on the membrane. FIG. 6 shows the results of a dot blot assay in which a male urine sample (control urine) was spiked with varying amounts of hCG and detected by radiolabeled H-42 RNA. As shown in FIG. 7, quantitation of the radioactivity on blots indicates that the amount of radiolabeled RNA retained correlates with the concentration of hCG. The signal saturates at high hCG concentration (>500 nM). Even at 1.9 nM hCG concentration, signal above background level was detected. Compared to control male urine (blots 1–3), the urine from a pregnant female (test urine) gave a distinct signal (blots 4–6) in an RNA dot blot assay (FIG. 8). The lack of signal above background level in the control blots (compared to buffer alone) demonstrates high specificity of the selected RNA ligand for hCG. In this assay, however, the intensity of the radioactive signal is sensitive to the salt concentration of the buffer in which the RNA is suspended. RNA suspended in relatively low salt TESM buffer (10 mM Tris-HCl, 0.1 mM EDTA, 100 mM NaCl and 2 MM $MgCl_2$ (pH 6.0)) gave a higher signal than that suspended in standard PBS buffer.

We claim:

1. A method for detecting the presence of a target compound in a complex mixture which may contain said target compound comprising:
   a) identifying a nucleic acid ligand from a candidate mixture of nucleic acids, said nucleic acid ligand being a ligand of said target compound, by the method comprising:
     i) contacting the candidate mixture with said target compound, wherein nucleic acids having an increased affinity to said target relative to the candidate mixture may be partitioned from the remainder of the candidate mixture;
     ii) partitioning the increased affinity nucleic acids from the remainder of the candidate mixture;
     iii) amplifying the increased affinity nucleic acids to yield a ligand-enriched mixture of nucleic acids; and
     iv) identifying said nucleic acid ligand;
   b) immobilizing complex mixture which may contain said target compound to a solid support;
   c) exposing said mixture to a nucleic acid ligand identified by the method of step (a) to said target compound wherein said nucleic acid ligand binds to said target compound forming a nucleic acid ligand:target compound complex; and
   d) detecting said nucleic acid ligand:target compound complex.

2. The method of claim 1 wherein said nucleic acid ligand comprises an enzyme linked to said nucleic acid ligand.

3. The method of claim 2 wherein detection is accomplished by addition of a substrate which said enzyme can hydrolyze and produce a measurable color.

4. The method of claim 2 wherein said enzyme is selected from the group consisting of horseradish peroxidase, alkaline phosphatase, and b-galactosidase.

5. The method of claim 1 wherein said solid support is selected from the group consisting of nitrocellulose, nylon, and charged paper.

6. The method of claim 1 wherein said target compound is a protein.

7. The method of claim 6 wherein said protein is selected from the group consisting of VEGF, hCG and hTSH.

8. The method of claim 1 wherein said complex mixture is a biological fluid.

9. The method of claim 8 wherein said biological fluid is selected from the group consisting of blood, plasma, serum, sputum, urine, semen, cerebrospinal fluid, bronchial aspirate, and macerated tissue.

10. The method of claim 1 wherein said detection is achieved by PCR amplification of said nucleic acid ligand.

11. The method of claim 10 wherein primers used for PCR amplification further comprise detection moieties.

12. The method of claim 11 wherein said detection moieties are selected from the group consisting of biotin and enzymes.

\* \* \* \* \*

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i x ) FEATURE:
        ( D ) OTHER INFORMATION: T's at positions 2-5 and
            29-34 are 2'deoxy
            phosphorothioate thymidine.

( i x ) FEATURE:
        ( D ) OTHER INFORMATION: C's at position 7-9 are 2'
            amino cytosine.

( i x ) FEATURE:
        ( D ) OTHER INFORMATION: A's at positions 6 and 17
            are 2'O- methyl adenine.

( i x ) FEATURE:
        ( D ) OTHER INFORMATION: G's at positions 14, 18,
            21, 24-27 and 29 are 2'

O-methyl- guanine (ix) FEATURE:
  (D) OTHER INFORMATION: U's at positions 10, 13, 16
    and 28 are 2'-amino
    uridine.

(xi) SEQUENCE DESCRIPTION: SEQ ID NO: 1:

NTTTTACCCU GAUGGUAGAC GCCGGGGUGT TTTT    34

(2) INFORMATION FOR SEQ ID NO: 2:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ix) FEATURE:
    (D) OTHER INFORMATION: A's at positions 2 and 13
      are 2'O- methyl adenine.

(ix) FEATURE:
    (D) OTHER INFORMATION: C's at positions 3-5 and 16
      are 2'amino cytosine.

(ix) FEATURE:
    (D) OTHER INFORMATION: U's at positions at 6, 9
      and 12 are 2'amino
      uridine.

(ix) FEATURE:
    (D) OTHER INFORMATION: G's at positions 10, 14,
      17, 20-23 and 25 are 2'
      O-methyl guanine.

(ix) FEATURE:
    (D) OTHER INFORMATION: T's at positions 26-27 are
      attached by a 3'3'linkage.

(xi) SEQUENCE DESCRIPTION: SEQ ID NO: 2:

NACCCUGAUG GUAGACGCCG GGGUGTT    27

(2) INFORMATION FOR SEQ ID NO: 3:

(i) SEQUENCE CHARACTERISTICS:
    (A) LENGTH: 71 base pairs
    (B) TYPE: nucleic acid
    (C) STRANDEDNESS: single
    (D) TOPOLOGY: linear (ix) FEATURE:
    (D) OTHER INFORMATION: All C's are 2'-amino
      cytosine.

(ix) FEATURE:
    (D) OTHER INFORMATION: All U's are 2'-amino
      uridine.

(xi) SEQUENCE DESCRIPTION: SEQ ID NO: 3:

GGGAGGACGA UGCGGAUGUU GGCAGCAGGG UCCGACGGCG UAACCUUGCC    50

AGCUGCAGAC GACUCGCCCG A    71

(2) INFORMATION FOR SEQ ID NO: 4:

(i) SEQUENCE CHARACTERISTICS:
    (A) LENGTH: 71 base pairs
    (B) TYPE: nucleic acid
    (C) STRANDEDNESS: single
    (D) TOPOLOGY: linear (ix) FEATURE:
    (D) OTHER INFORMATION: All C's are 2'-amino cytosine.

(ix) FEATURE:
    (D) OTHER INFORMATION: All U's are 2'-amino uridine.

(xi) SEQUENCE DESCRIPTION: SEQ ID NO: 4:

```
GGGAGGACGA  UGCGGACAAG  GGCCUGAGUG  UGGAGGGCAC  GUGGAGGGGA      50
CUGGCCAGAC  GACUCGCCCG  A                                       71
```